United States Patent
Lindholm et al.

[11] Patent Number: 5,949,000
[45] Date of Patent: Sep. 7, 1999

[54] SAMPLING DEVICE FOR USE IN PERFORMING THERMAL ANALYSIS OF SOLIDIFYING METAL

[75] Inventors: Ragnar Lindholm, Bromma, Sweden; Torsten Lindholm, Golfe Juan, France; Mikael Thoren, Stockholm; Patrik Popelar, Katrineholm, both of Sweden

[73] Assignee: Sintercast AB, Stockholm, Sweden

[21] Appl. No.: 08/875,379

[22] PCT Filed: Jan. 25, 1996

[86] PCT No.: PCT/SE96/00077

§ 371 Date: Jun. 25, 1997

§ 102(e) Date: Jun. 25, 1997

[87] PCT Pub. No.: WO96/23206

PCT Pub. Date: Aug. 1, 1996

[30] Foreign Application Priority Data

Jan. 27, 1995 [SE] Sweden ................... 9500297-8

[51] Int. Cl.⁶ ........................................... G01N 37/00
[52] U.S. Cl. .................. 73/864.91; 374/139; 374/157
[58] Field of Search .................... 73/864.91, 863; 374/26, 140, 139, 157, 12, 158, 208, 209; 420/28, 31

[56] References Cited

U.S. PATENT DOCUMENTS

| | | | |
|---|---|---|---|
| 3,695,093 | 10/1972 | Hummel et al. | 374/25 |
| 3,943,774 | 3/1976 | Pollanz | 374/28 |
| 3,994,164 | 11/1976 | Regenass et al. | 374/31 |
| 4,159,307 | 6/1979 | Shigeyasu et al. | 422/215 |
| 4,456,389 | 6/1984 | Regnass et al. | 374/31 |
| 4,667,725 | 5/1987 | Bäckerud. | |
| 4,804,274 | 2/1989 | Green | 374/25 |
| 5,100,244 | 3/1992 | Kniebes | 374/36 |

FOREIGN PATENT DOCUMENTS

| | | |
|---|---|---|
| 150996 | 10/1987 | Denmark. |
| 350 606 | 10/1972 | Sweden. |

OTHER PUBLICATIONS

E. Schürmann, et al., "Prinzip Und Probleme Der Thermischen Analyse Einer Kleinen Im Sandtiegel Erstarrenden Legierten Metallprobe", Giesserei, vol. 76, No. 9, May 1989, pp. 287–297.

*Primary Examiner*—Hezron Williams
*Assistant Examiner*—Nashmiya Fayyaz
*Attorney, Agent, or Firm*—Pillsbury, Madison & Sutro, LLP

[57] ABSTRACT

A sampling device for use when performing a thermal analysis of a sample of molten metal solidifying from a melt, includes a double-walled container having an upwardly opening mouth and a part-spherically curved bottom, A closed space between the walls is thermally insulated. A tubular holder is supported to extend from the mouth substantially to the bottom of the container, for receiving a temperature sensor. By preference at least one wall of the container is treated or coated to reduce thermal emissivity.

4 Claims, 2 Drawing Sheets

SAMPLING DEVICE FOR USE IN PERFORMING THERMAL ANALYSIS OF SOLIDIFYING METAL

This application is the national phase of international application PCT/SE96/00077 filed Jan. 25, 1996 which designated the U.S.

INTRODUCTION

The present invention relates to a sampling device for thermal analysis of solidifying metal, comprising a container intended to contain a sample quantity of liquid metal during analysis, and at least one sensor for thermal analysis, the sensor(s) being intended to be immersed in the solidifying metal sample quantity during analysis. The invention also relates to the sample container of the sampling device. The device and container are primarily intended for thermal analysis in connection with production of cast iron, in particular in connection with production of Compacted Graphite Iron, below abbreviated as CGI.

TECHNICAL FIELD

Thermal analysis is a technique which monitors the variations in the temperature change of certain molten substances during solidification in order to determine the microstructure and hence properties of the substances in solid form. This is basically accomplished by taking a sample from a melt, bringing it into a test vessel and recording and evaluating the time-dependent temperature change in the sample during solidification, by means of temperature responsive means, such as thermocouples or pyrometers or other such devices known to a person skilled in the art.

When using thermal analysis for controlling solidification processes in molten materials such as cast-iron, e.g. CGI, or aluminium alloys, a most critical issue is to quickly bring the test vessel and the sample as close to thermal equilibrium as possible, and to provide for a controlled, even and reproducible rate of heat removal from the sample. The reason for this is to make it possible to measure temperature changes during phase transformations, e.g. supercooling and latent heat evolved during the nucleation and growth of primary and secondary solidification phases, the knowledge of which is essential in order to control certain solidification processes.

BACKGROUND ART

One technique to establish thermal equilibrium and to achieve a controlled heat removal rate is taught by SE 350,606 and comprises immersing the sampling vessel in a molten bath of the metal to be analyzed or heating the vessel in some other way, in order to establish thermal equilibrium between the sampling vessel and its contents at a temperature above the temperature of crystallisation prior to commencement of the cooling process of the thermal analysis. A sampling vessel adapted for this technique is also disclosed, that vessel being made of graphite, for use in aluminium melts, or made of a ceramic material, when intended for use in melt cast iron.

Another sampling vessel for thermal analysis, though only directed at aluminium alloys, is disclosed in DK-B-150,996. That vessel comprises a small crucible of steel sheet, provided with a plug of thermally insulating material, e.g. core sand, at the bottom.

Apart from the vessels mentioned above, there are several other sample vessels of the similar kind occuring in the art. A common drawback for these vessels is that they all are made of, or comprise as an essential part, materials such as graphite, furan sand, core sand or refractory cement; these materials are all known to be difficult to work. The available manufacturing techniques are slow and have considerable quality problems due to the nature of the material. Although it would be desirable to provide for various vessel features, giving a variety of different heat removal characteristics, in order to produce sampling vessels adapted for thermal analysis of different metals and alloys, this has hitherto not been possible, since the limited choice of materials for producing such vessels has seriously restricted the latitude to select among these characteristics. Likewise, it has been difficult to provide sampling vessels that give cooling rates that are sufficiently accurate and repeatable to fulfil the requirements of thermal analysis, due to the constricted selection of characteristics obtainable.

Regarding the sampling vessels of immersion type, i.e. the ones that are immersed in the bulk of the melt metal when sampling, a special drawback is the risk of thermal shock cracking, particularly when the vessels are made of ceramic materials. Sampling vessels made according to prior art of course also suffer from the risk of contamination the molten metal sample.

DISCLOSURE OF THE INVENTION

It is an object of the present invention to provide a sampling device, and in particular a container for such a device, of the kind mentioned in the introduction, by means of which the drawbacks stated above are overcome.

The container of the sampling device shows resemblance to a Dewar vessel, and in some embodiments it may actually be a Dewar vessel, i.e. a double-walled vessel with an evacuated space between the walls that has an extremly low thermal conductivity. However, in general the space between the inner and the outer walls of the container is not evacuated, but more or less filled with a thermally insulating medium, preferably a gas, most preferably air.

The inner wall of the container is preferably made rather thin and/or of a material with a low specific thermal capacity, in order to impart a desirable low total thermal capacity to the inner wall. In addition to this, the inner wall has preferably a high total heat transfer coefficient, providing for thermal equilibrium between the wall and a molten metal sample quantity, that is poured in the sampling container, to be established in a very short period of time. As the thermal capacity of the inner wall is low, the required amount of heat that has to be transferred from the sample quantity to the wall in order to equalize the temperature of the sample quantity and the wall will also be low; and as the total heat transfer coefficient is high, the time required to transfer the amount of heat will be short.

The inner wall may be made of any material that has the thermal properties stated above while being both thermally and chemically stable in the molten metal being sampled. Selection of a specific material may be governed by the kind of thermal analysis that is to be accomplished, and by the metals or alloys that are to be analyzed. Typically a metal or alloy is used. Materials that are inexpensive and easy to work, especially steel, are preferred.

The advantages provided by the inner wall would however be absent had it not been for the presence of the outer wall. Heat issuing from the exterior surface of the inner wall must not be immediately let out into the ambient atmosphere, as this would make it very difficult to accomplish a controlled, even and reproducible heat removal rate.

Thus, the purpose of the outer wall is to define, together with the inner wall, a space between the walls that has a low total heat transfer coefficient, i.e. a space through which the heat transfer rate is low.

By selecting and fully or partly filling the space with a suitable medium, and/or by altering the thickness of the space, it is possible to adapt the heat removal rate of the sampling device to the values required by various forms of thermal analysis. Said medium may be any known and suitable heat insulating medium, such as, for instance, sand, vermiculite, mica, magnesia, chlorite, various ceramics or combinations thereof, but is preferably a gas; air is most preferred as it is available in large amounts at no cost.

A substansive part of the heat transmitted from the inner wall to the outer wall of the sampling vessel is due to radiation. Thus, it is possible to regulate the rate of heat removed from the inner wall to the outer wall by designing a vessel having an outer wall with a surface area that is relatively big in relation to the surface area of the inner wall; the distance between the inner and the outer wall may be an important parameter in this context. Alternatively, one may alter the color and/or the surface finish to modify the radiation behavior.

When using the double-cup method of controlling heat transfer away from a contained sample, the gap between the two cups plays a crucial role. When this gap is evacuated, or filled with a transparent liquid, like air, radiation will be an important heat transfer mechanism. As temperature of the contained sample increses, radiation will be of increasing importance since its effect increases with the fourth power of absolute temperature.

Radiation heat transfer is also limited by surface property called emissivity. A perfect surface emitter is termed a blackbody, and has an emissivity of 1. Real surfaces will emit less energy, and are assigned an emissivity between 0 and 1.

By altering the surface treatment, or coating a surface the overall heat transferred from a surface may be altered considerably. Polished metallic surfaces have very low emissivities, and radiate the least amount of heat. Other possible surface treatments include brushing, etching, and sand; blasting and chemical treatments.

Coated surfaces will, for the most part, assume the radiation properties of the coating. High temperature coatings that can be used for this purpose include sintered and plasma sprayed ceramics based on alumina, magnesia, zirconia, silicon carbide, silicon nitride, carbon, boron nitride, and silica. There are also several commercially available foundry coatings based on boron nitride, zirconia and carbon which will work well as a radiation control coating.

The heat removal rate may also be controlled by adapting the size and/or shape of the sampling container to meet certain thermal analysis requirements, highlighting yet another important advantage of the present invention, namely the ease to impart a specific size and/or shape to the container of the present invention, e.g. by deep drawing and similar techniques well-known in the art. Preferably, the container has the form of a cup, the geometry of which is at least partly spherical, the bottom of which having a semisperical shape in order to ensure uniform heat loss in all directions. Additionally, the sample must hang freely, rather than being supported by a stand, which would interfere with the uniformity of heat loss.

The interior surface of the inner wall of the container is preferably coated with a protective coating in order to protect the wall from dissolving when confronted with the hot liquid metal sample. Such protective coating could also be applied to the exterior surface of the outer wall, particularly if the container is intended to be immersed in in hot liquid metal when sampling. The protective coating could be a refractory oxide, such as alumina, for instance. Although the sampling device of the present invention in a basic embodiment may only consist of a container of a double-walled type and a single thermal analysis sensor, it will generally also comprise some kind of sensor support member, the purpose of which is to hold the sensor in position during at least some part of the analysis. The support member may have the form of a hood, intended to cover the mouth of the sampling container during analysis in order to protect the sensor-sample system from external disturbance; the hood may be equipped with a device for supplying inert gas, optionally heated, in case the surface of the molten metal sample has to be protected from the ambient atmosphere.

The sensors for thermal analysis are generally thermocouples, although the present invention is not limited in that sense; any kind of sensor suited for thermal analysis of solidifying metal may form part of the invention.

The sampling device is preferably adapted for use in connection with production of CGI according to the method disclosed in U.S. Pat. No. 4,667,725 (Backerud). In this embodiment the device comprises two temperature; responsive means or sensors, of which one is placed in the center of the sample quantity and the other in the molten material at a location close to the interior surface of the inner wall of the container. The protective coating, if any, in this embodiment is preferably a coating of the kind appearing in WO 92/06809, i.e. a coating comprising a substance which will lower the concentration of dissolved elementary magnesium in the melt in the vicinity of the vessel wall by at least 0.003%; a coating of this latter kind can, for instance, contain at least 10 percent by weight of oxides of silicon, manganese or iron, or at least 0.5 percent by weight of oxides of potassium and sodium.

In a particularly preferred embodiment, designed for CGI production, the device comprises a protective closed end tube that is immersed in the solidifying metal during analysis, a first thermocouple gauge located in proximity of the closed end of the tube during analysis, the first thermocouple being removably insertable in the protective tube, and a second thermocouple gauge also being removably insertable in the protective tube. The thermocouples are sufficiently spaced apart to minimize the exchange of heat between them during analysis. This embodiment is particularly advantageous in that thermocouples can be reused for a number of measurements, instead of being consumed during just one single analysis operation. Preferably, the container is substantially symmetrical about a vertical axis, and the closed end tube is positioned coaxially with that vertical axis; in that way problems regarding impact of side forces, appearing when the sample solidifies and incurs volumetric changes, on the thermocouple located closest to the inner wall are reduced.

BRIEF DESCRIPTION OF DRAWINGS

The invention will now be described in more detail with reference to the accompanying drawings, in which.

DETAILED DESCRIPTION

Figure 1:
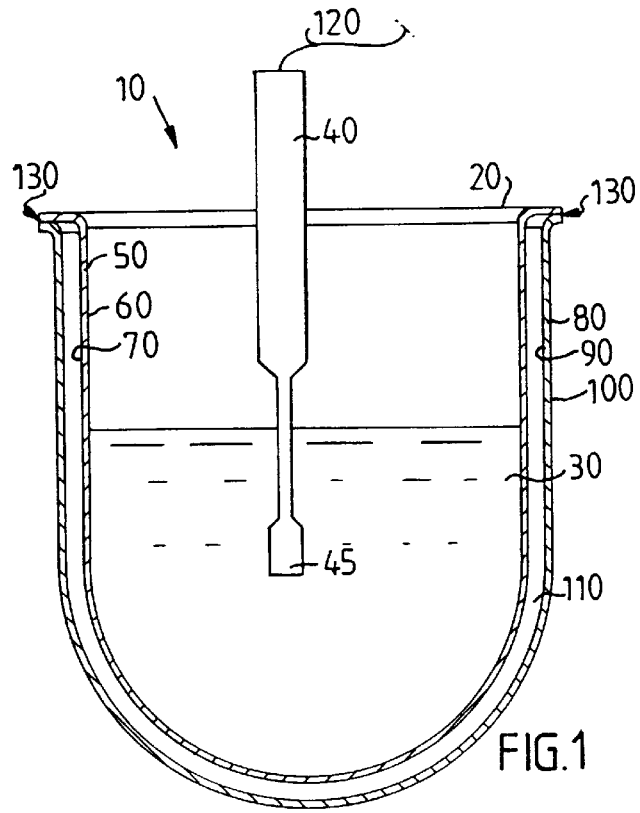
FIG. 1 is a schematic cross section through a sampling device according to a basic embodiment of the present invention.

FIG. 1 shows a sampling device 10, comprising a bowl; shaped sampling container 20, filled with a sample quantity 30 of molten metal under solidification, and temperature responsive sensor means 40 for thermal analysis. The gauge part 45 of the sensor 40, which in the present case is a thermocouple device, is immersed in the sample quantity 30. The container 20 consists of an inner wall 50 and an outer wall 80, both made of thin steel sheet, and in between these walls a space 110, defined by the exterior surface 70 of the inner wall 50 and the interior surface 90 of the outer wall 80. A weld 130 serves to join the walls at the mouth of the container 20. The weld 130 could be a continous seam or a spot weld; optionally, the walls could be joined by folding instead of—or complementary to—welding. The space 110 is filled with air. In the illustrated embodiment, a protective coating according to WO 92/06809 is applied to the interior surface 60 of the inner wall 50 and the exterior surface 100 of the outer wall 80 to protect the thin steel sheet walls from dissolving when confronted with hot liquid metal. The sensor 40 is connected to a thermal analysis evaluation equipment (not shown) by a cable 120, through which measuring signals from the gauge part 45 are transmitted to said equipment for analysis.

Figure 2:
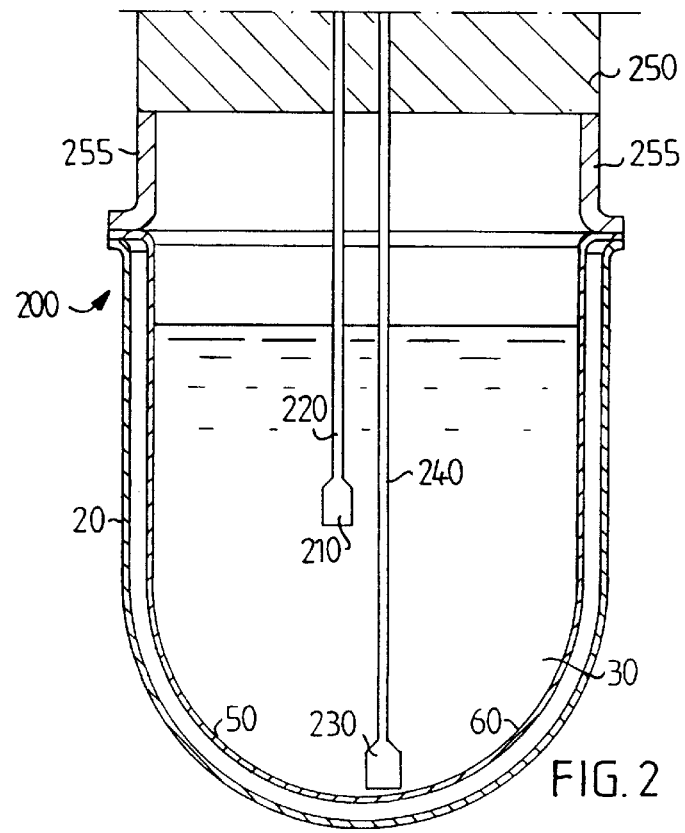
FIG. 2 is a cross section through a part of a sampling device according to an embodiment of the invention that is designed for use in connection with CGI production.

A sampling device 200 for use in CGI production, partly shown in FIG. 2, comprises the same kind of container as the device shown in FIG. 1. Device 200 is however equipped with two sensors, arranged essentially in accordance with the teachings of U.S. Pat. No. 4,667,725 mentioned above: the gauge part 210 of the first temperature responsive sensor 220 is placed in the center of the sample quantity 30, and the gauge part 230 of the second sensor 240 is placed at a location close to the interior surface 60 of the inner wall 50. A sensor support member 250 is provided to hold the sensors 220, 240 in position during analysis. The sensor support member 250 is connected to the container via legs 255, between which liquid metal flows down into the container when immersed.

Figure 3:
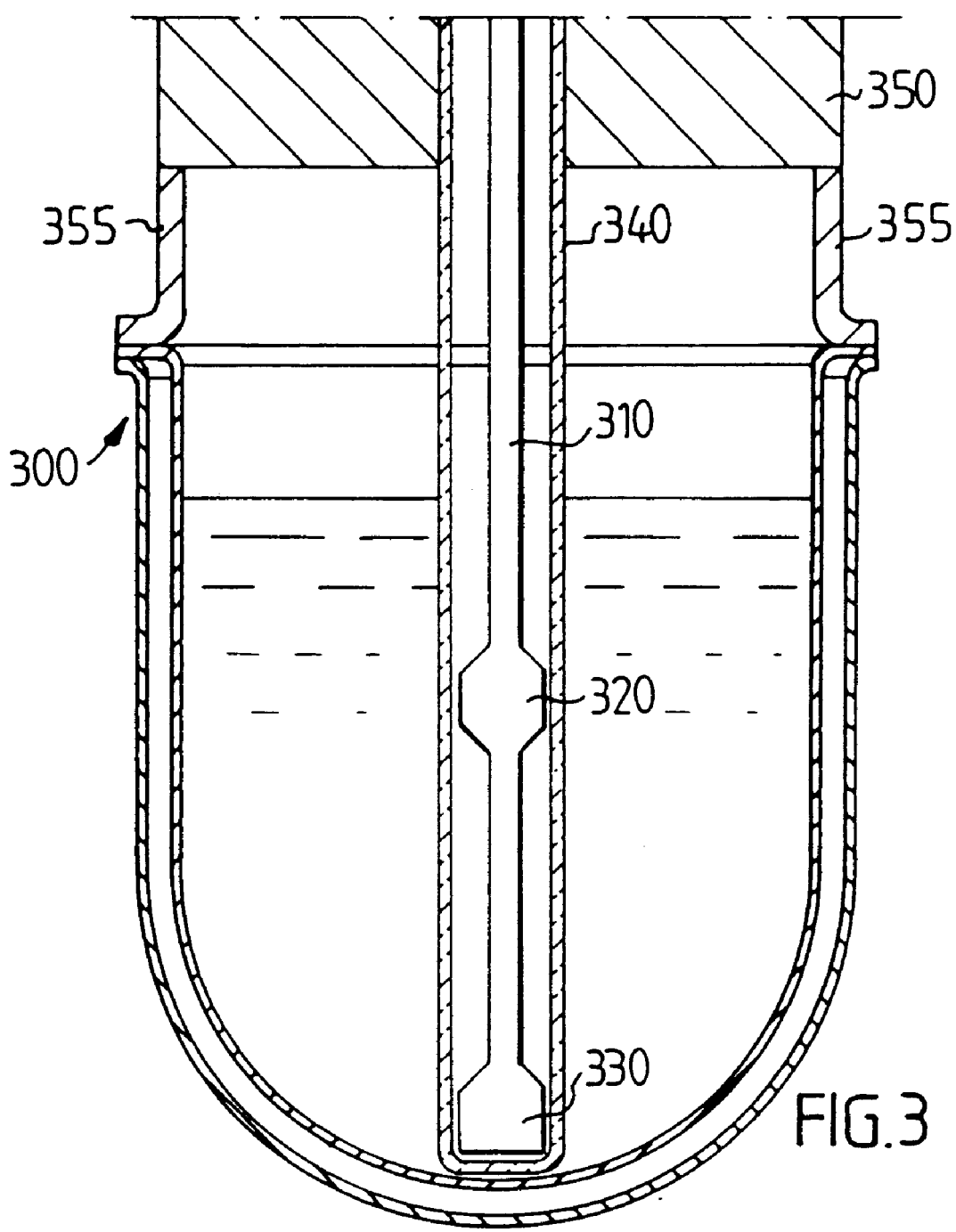
FIG. 3 illustrates, also in cross section, a particularly preferred embodiment of the invention, also designed for CGI production, equipped with a protective closed end tube for the thermocouples.

FIG. 3 shows a part of a sampling device 300 in accordance with an especially advantageous embodiment of the present invention. Like the device shown in FIG. 2, device 300 is intended for use in CGI production, but instead of two separate sensors this device is equipped with a single sensor member 310, though comprising two thermocouple gauges 320, 330 basically located in accordance with the teachings of U.S. Pat. No. 4,667,725. The sensor member 310 is removably inserted in a protective tubing 340 made of steel, ceramics, glass or any other suitable material. A support member 350 is provided to hold the protective tubing 340 in position during the thermal analysis. Similar to the previous case, the support member 350 is connected to the container 20 by means of legs 355.

It will be understood that it lies within the expertise of a person skilled in this art, and within the scope of the present invention, to make suitable modifications to the aforedescribed sampling devices, and that the said device is not limited for use in production of CGI or other forms of cast iron only, but may also be used in production of a variety of other metals.

We claim:

1. A sampling device for performing a thermal analysis of a sample quantity of molten metal solidifying from a melt, comprising:

a container having an upwardly open mouth and a part-spherically curved bottom, said container arranged to contain the sample quantity of molten metal, for thermal analysis, said container including an inner wall having an inner surface arranged to face the sample quantity during thermal analysis, an outer wall having an exterior surface arranged to face ambient atmosphere, and an interior surface, said inner and outer walls being joined at said mouth of said container, to enclose a space, bounded by said interior surface, between said inner and outer walls, said space being occupied by a thermally insulating medium, and said inner wall being made of a metal or metal alloy;

a protective tubing member received in said container extending from said mouth substantially to said bottom;

a support member hangingly supporting said protective tubing member relative to said container without being disposed in direct contact with the container; and a temperature sensor adapted to measure temperature changes for thermal analysis of the sample quantity of the molten metal, which sensor is removably received in said protective tubing member.

2. The sampling device of claim 1, wherein:

said inner wall of said container is made of steel.

3. The sampling device of claim 1, wherein:

at least one of said inner and exterior surfaces has a thermal emissivity which is reduced by having been subjected to a treatment selected from brushing, etching, sand-blasting and chemical contact.

4. The sampling device of claim 1, wherein;

at least one of said inner and exterior surfaces has a thermal emissivity which is reduced by having been received by plasma spraying or sintering, an applied ceramics coating based on alumina, magnesia, zirconia, silicon carbide, silicon nitride, carbon, boron nitride and silica.

* * * * *